United States Patent
Tumanov

(10) Patent No.: US 9,623,130 B2
(45) Date of Patent: Apr. 18, 2017

(54) DISINFECTING TOUCH-BASED SCREEN AUTOMATICALLY

(71) Applicant: Microsoft Technology Licensing, LLC, Redmond, WA (US)

(72) Inventor: Ilya Tumanov, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 245 days.

(21) Appl. No.: 14/637,382

(22) Filed: Mar. 3, 2015

(65) Prior Publication Data

US 2015/0174276 A1    Jun. 25, 2015

Related U.S. Application Data

(62) Division of application No. 13/210,625, filed on Aug. 16, 2011, now Pat. No. 8,999,237.

(51) Int. Cl.
| | |
|---|---|
| *A61L 2/00* | (2006.01) |
| *A61L 2/10* | (2006.01) |
| *A61L 2/24* | (2006.01) |
| *G06F 1/16* | (2006.01) |
| *G06F 3/041* | (2006.01) |
| *H04M 1/17* | (2006.01) |

(52) U.S. Cl.
CPC  *A61L 2/10* (2013.01); *A61L 2/24* (2013.01); *G06F 1/1607* (2013.01); *G06F 1/1643* (2013.01); *G06F 3/041* (2013.01); *G06F 3/0412* (2013.01); *H04M 1/17* (2013.01)

(58) Field of Classification Search
CPC .................................. A61L 2/10; G06F 1/643
USPC ......................................... 422/24; 250/492.1
See application file for complete search history.

(56) References Cited

U.S. PATENT DOCUMENTS

| | | |
|---|---|---|
| 6,713,027 B2 | 3/2004 | McNulty, Jr. |
| 7,598,501 B2 | 10/2009 | Jones |
| 7,692,159 B2 | 4/2010 | Lane et al. |
| 2009/0252646 A1 | 10/2009 | Holden et al. |
| 2010/0028201 A1 | 2/2010 | Neister |
| 2010/0127189 A1 | 5/2010 | Boyarsky et al. |
| 2010/0235787 A1 | 9/2010 | Couse et al. |
| 2011/0291995 A1 | 12/2011 | Shr et al. |

OTHER PUBLICATIONS

Non-Final Office Action for U.S. Appl. No. 13/210,625, mailed on Jun. 11 2014 and filed Aug. 16, 2011.
"Cellphone sanitizer hits the market", Retrieved at <<http://wirelessfederation.com/news/28704-cellphone-sanitizer-hits-the-market/>>, Oct. 21, 2010, pp. 5.
"New Motorola Phone Fights Dirty Germs", Retrieved at <<http://www.textually.org/textblog/mt_search.php?IncludeBlogs=&search=gems>>, Retrieved Date: Jun. 22, 2011, pp. 27.

*Primary Examiner* — Kevin Joyner
(74) *Attorney, Agent, or Firm* — Turk IP Law, LLC

(57) ABSTRACT

A UV and visible light transparent film material is secured onto or within a touch-based screen to automatically disinfect the external surface. UV light is emitted from a UV light source into an edge of the transparent film material in order to transfer the UV light through the transparent film material while remaining in the transparent film material through total internal reflection effect. Some UV light exits the transparent film material at points of contact to disinfect fingertips and immediate surrounding areas through the frustrated total internal reflection effect.

20 Claims, 6 Drawing Sheets

DISINFECTING TOUCH-BASED SCREEN AUTOMATICALLY

This Application is a divisional under 35 U.S.C. §121 of U.S. patent application Ser. No. 13/210,625 filed on Aug. 16, 2011, now U.S. Pat. No. 8,999,237. The U.S. Patent Application is herein incorporated by reference in its entirety.

BACKGROUND

With the development and wide use of computing and networking technologies, personal and business communications have proliferated in quantity and quality. In modern world, integrated network capable devices have enabled an enhanced and feature rich life. Advances in manufacturing processes and computing capacity have produced devices capable of diverse tasks and features not previously imagined. Such devices partake an ever increasing share in users daily activities. As a result, long list of devices are susceptible to transmit and carry disease causing agents as a result of physical user interaction.

Disease causing agents such as bacteria, viruses, etc. are transmitted by devices that users interact with daily. Touch-based screens are becoming an ever prevalent presence in variety of user interaction capable devices. Surfaces of these touch-based screens are riddled with finger prints and other interaction remnants carrying potential disease causing agents. Frequent use and trading among users also are substantial problems in continued transmission of disease causing agents from user to device, device to user and other users. Limiting exposure by enforcing single user devices does not eliminate the pathogenic exposure and severely limits the utility of such devices. Single user devices are also resource wasteful and may not suit all functional requirements. In some cases such as a public terminal, single user restriction may not be a solution. Solutions such as removable screen covers are inconvenient with costly if frequently replaced.

SUMMARY

This summary is provided to introduce a selection of concepts in a simplified form that are further described below in the Detailed Description. This summary is not intended to exclusively identify key features or essential features of the claimed subject matter, nor is it intended as an aid in determining the scope of the claimed subject matter.

Embodiments are directed to disinfecting a touch-based screen automatically with ultra violet (UV) light. According to some embodiments, a disinfection controller may detect a predetermined event to trigger disinfection of a touch-based screen. The controller may activate UV light source(s) located on edge(s) of a transparent film material substantially covering the touch-based screen. The light source(s) may emit UV light through the transparent film material to disinfect the touch-based screen.

These and other features and advantages will be apparent from a reading of the following detailed description and a review of the associated drawings. It is to be understood that both the foregoing general description and the following detailed description are explanatory and do not restrict aspects as claimed.

DETAILED DESCRIPTION

Figure 1:
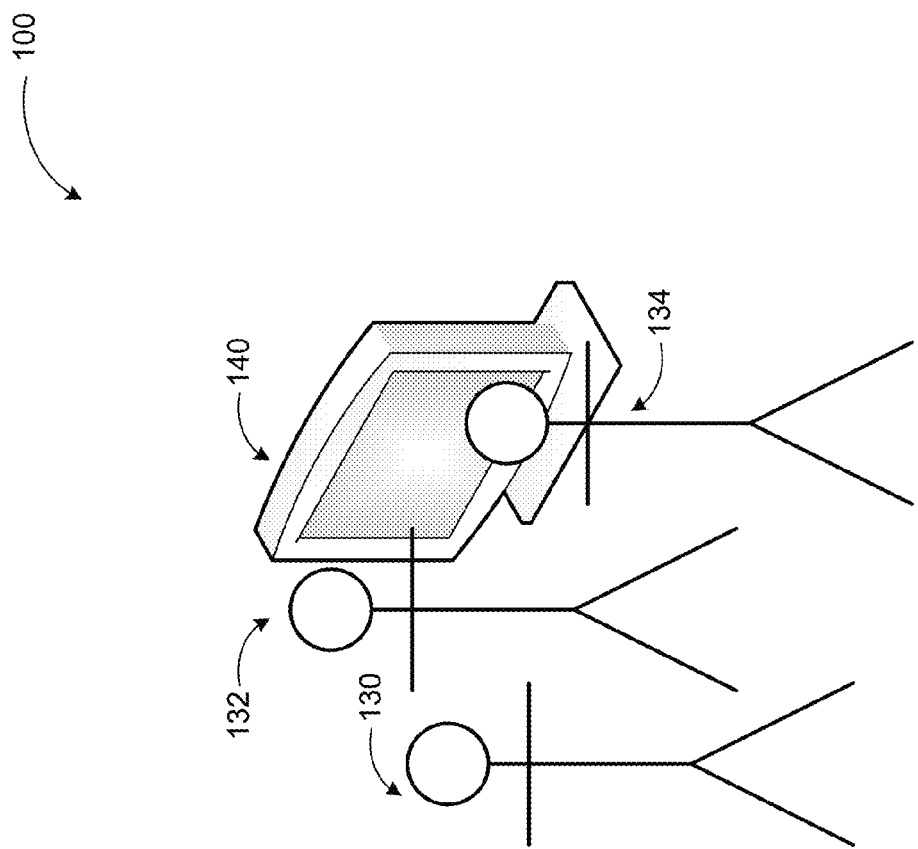
FIG. 1 illustrates a conceptual diagram displaying use scenarios for automatically disinfecting touch-based screens.
Figure 1:
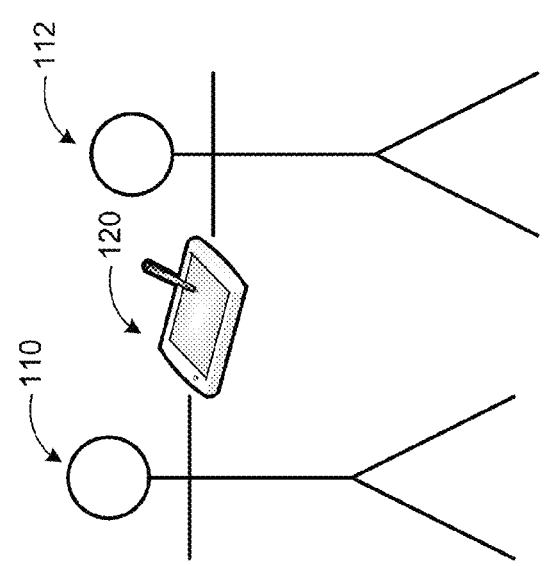

As briefly described above, a touch-based screen may be automatically disinfected using ultra violet (UV) light. Detection of a predetermined event by a disinfection controller may trigger the disinfection of the touch-based screen. In an embodiment, the predetermined event may be a touch event. Upon detecting the predetermined event, the controller may activate UV light source(s) located on the edge(s) of a transparent film material to illuminate the transparent film material. Emitted UV light may disinfect external surface of the transparent film material secured onto a display surface of the touch-based screen. In an alternate embodiment, a user's fingertips may also be disinfected when some UV light exits the transparent film material because of the frustrated total internal reflection (FTIR) effect.

In the following detailed description, references are made to the accompanying drawings that form a part hereof, and in which are shown by way of illustrations specific embodiments or examples. These aspects may be combined, other aspects may be utilized, and structural changes may be made without departing from the spirit or scope of the present disclosure. The following detailed description is therefore not to be taken in a limiting sense, and the scope of the present invention is defined by the appended claims and their equivalents.

While the embodiments will be described in the general context of program modules that execute in conjunction with an application program that runs on an operating system on a computing device, those skilled in the art will recognize that aspects may also be implemented in combination with other program modules.

Generally, program modules include routines, programs, components, data structures, and other types of structures that perform particular tasks or implement particular abstract data types. Moreover, those skilled in the art will appreciate that embodiments may be practiced with other computer system configurations, including hand-held devices, multi-processor systems, microprocessor-based or programmable consumer electronics, minicomputers, mainframe computers, and comparable computing devices. Embodiments may also be practiced in distributed computing environments where tasks are performed by remote processing devices that are linked through a communications network. In a distributed computing environment, program modules may be located in both local and remote memory storage devices.

Embodiments may be implemented as a computer-implemented process (method), a computing system, or as an article of manufacture, such as a computer program product or computer readable media. The computer program product may be a computer storage medium readable by a computer system and encoding a computer program that comprises instructions for causing a computer or computing system to perform example process(es). The computer-readable storage medium is a computer-readable memory device. The computer-readable storage medium can for example be implemented via one or more of a volatile computer memory, a non-volatile memory, a hard drive, a flash drive, a floppy disk, or a compact disk, and comparable media.

According to embodiments, UV light may be used to disinfect the external surface of a transparent material secured onto a display surface of a touch-based screen. UV light in range of about 200-300 nm may be used by a device associated with the touch-based screen to kill bacteria, viruses, and other disease causing agents. Touch-based screens may be deployed in a variety of devices including but not exclusive to smart phones, tablets, laptops, monitors, etc. Small size of the touch-based screen may minimize power required to disinfect the external surface of the transparent film material compared to industrial applications such as hospital disinfection utilizing 10-40 W UV lamps for disinfecting large rooms. Additionally, the external surface may be disinfected by UV light emitted from LED based or mercury filled gas discharge lamp UV light sources.

Throughout this specification, the term "platform" may be a combination of software and hardware components for automatically disinfecting a touch-based screen. Examples of platforms include, but are not limited to a device associated with a touch-based screen, an application executed on the device, and comparable systems. The term "server" generally refers to a computing device executing one or more software programs typically in a networked environment. However, a server may also be implemented as a virtual server (software programs) executed on one or more computing devices viewed as a server on the network.

FIG. 1 illustrates a conceptual diagram displaying use scenarios for automatically disinfecting touch-based screens. Diagram 100 illustrates multiple scenarios where automatic disinfection of a device associated with a touch-based screen may stop transmission of disease agents. User 110 may share a tablet device 120 with user 112. In such a scenario, automatic disinfection may prevent user 112 from exposure to user 110's potential disease causing agents. Alternatively, users 130, 132, and 134 may interact with a monitor 140 and associated touch-based screen. Automatic disinfection of the monitor's touch-based screen may prevent exposure to disease causing agents.

Integral to the disinfection process is a transparent film material secured onto a display surface of touch-based screens. The transparent film material may be transparent to UV and visible light. The UV light may be transmitted at a critical angle from the edge(s) of the transparent film material to reflect the UV light back into the transparent film material while containing the UV light within the transparent film material.

The transparent film material may be substantially covering a display surface of the touch-based screen. An example may be covering an entire display surface of the touch-based screen. The transparent film material may serve as a user contact surface. As a result, the external surface of the transparent film material may be disinfected frequently to prevent spreading of disease agents.

Optionally, optical index matching gel may be used between the UV light source(s) and edge(s) of the transparent film material to allow more UV light to enter the transparent film material. Addition of the gel may allow for low power UV light source(s) further maximizing safety. Safety may also be maximized by lowering power to the UV light source(s) and minimizing accidental exposure to UV light.

Figure 2:
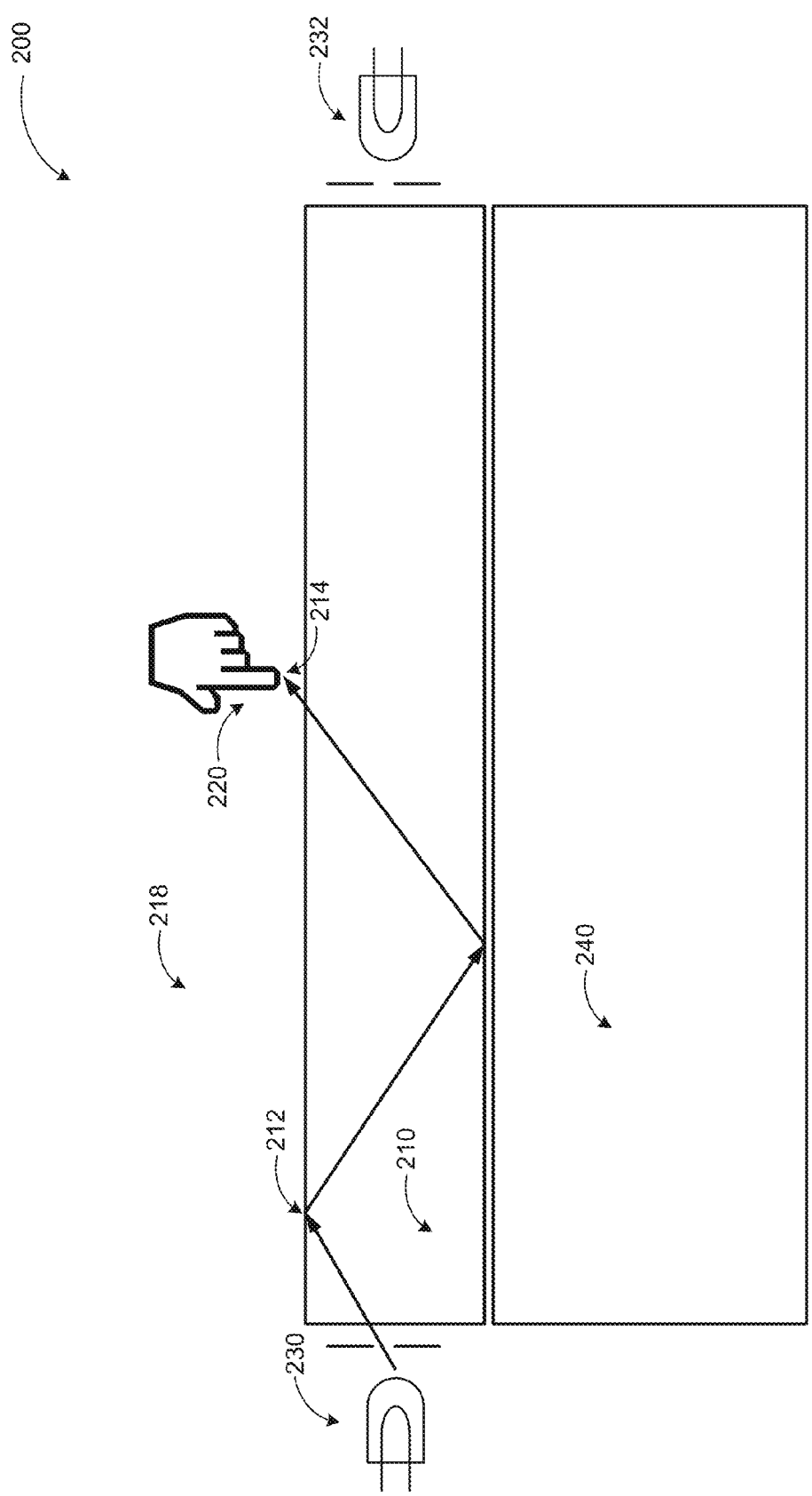
FIG. 2 is a conceptual diagram illustrating a touch-based screen configured to automatically disinfect its surface.

FIG. 2 is a conceptual diagram illustrating a touch-based screen configured to automatically disinfect its surface. One or more UV light sources 230 and 232 may be emitting UV light into the transparent film material through the transparent film material's edges. As previously stated, the UV light sources may be LED based or mercury filled gas discharge lamps. The transparent film material 210 may be transparent for UV light in about 200 nm to about 300 nm wavelength range as well as visible light range. The visible light may be in the 390 nm to 750 nm wavelength range. The transparent film material 210 may be quartz glass, UV transparent plastic or other similar materials. Additionally, the transparent film material 210 may be thin. In an example implementation, the transparent film material 210 may have a thickness of less than 1 millimeter.

Exposure to UV light is generally harmful. According to embodiments, users should not be exposed to UV light except for designated contact points which are subject to disinfection. In an example scenario, fingertips and immediate surrounding areas may be exposed to UV light because fingers have thicker skin and they are less susceptible to UV light. In other embodiments, exposure to the UV light may be further limited by shutting down UV light source on predetermined events such as timer expiration.

In an embodiment, total reflection effect may be demonstrated by the reflection of the UV light at point 212. UV light may not exit the transparent film material 210 when an angle of traversal (measured from normal to a surface of the transparent film material 210) is larger than the critical angle for specific materials (e.g.: air 218 and the transparent film material 210).

Accordingly, $\theta = \arcsin(n_2/m_2)$ where $n_2$ is a refractive index of air 218 (1.0 for air) and $m_2$ is a refractive index for the transparent film material 210 (1.45 for quartz glass). In an example scenario, the critical angle for emitting UV light from the edge of the transparent film material 210 may be 43 degrees using air 218 and quartz glass. Optical apertures or other optical devices may be used to ensure UV light may not exit the transparent film material 210. UV light may be reflected back into the transparent film material 210 as shown in point 212 when emitted at a critical angle.

Frustrated total internal reflection (FTIR) effect refers to when a user's finger 220 may be touching or be in near proximity to the external surface of the transparent film material 210 at point 214. FTIR happens when optimal medium with higher refractive index than air (1.4 for human skin) may be touching or near to the external surface. Touching or near proximity to the external surface may allow for some UV light to exit the transparent film material onto the user's contact points such as fingertips and immediate surrounding areas. As a result, exiting UV light may disinfect the contacting fingertips and immediate surrounding areas including external surface of the transparent film material potentially carrying decease causing agents. Furthermore, additional layer of flexible material may be added on top of the external surface of the transparent film material 210 to improve transfer of UV light from the transparent film material to the fingertips. The flexible material may behave similarly to liquid in immersion optics.

Figure 3:
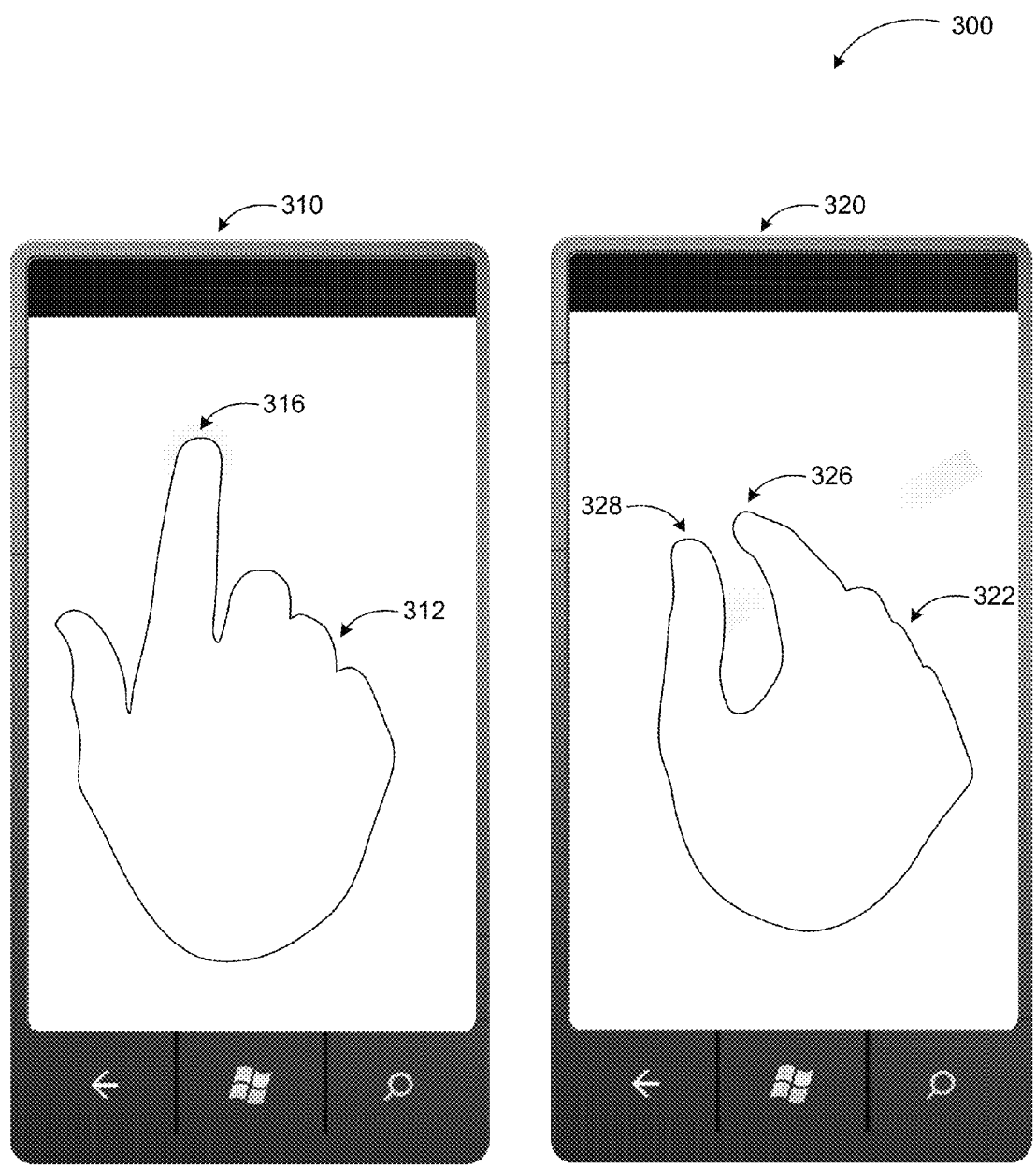
FIG. 3 illustrates example devices with a touch-based screen configured to automatically disinfect the screen's surface and fingertips interacting with the surface.

FIG. 3 illustrates example devices with a touch-based screen configured to automatically disinfect the screen surface and fingertips interacting with the surface. Diagram 300 displays example disinfection scenarios according to use.

Mobile device 310 may have a touch-based screen capable of disinfecting its external surface. A transparent film material may transfer UV light disinfecting the external surface of the transparent material secured onto a display surface of the touch-based screen as the user touches it. Additionally when a user touches the transparent film material at point 316 with hand 312, UV light may exit the transparent film material and disinfect the fingertips and immediate surrounding areas of the fingertips at contact point 316.

In an alternate embodiment, a user may contact the external surface of the transparent film material secured onto a display surface of the touch-based screen of the mobile device 320 with hand 322. A transparent film material may transfer UV light for disinfection. The UV light may exit the transparent film material through the FTIR effect as described above and disinfect fingertips and immediate surrounding area of fingertips at contact points 326 and 328.

In another embodiment, the transparent film material is thin and flexible. Flexible transparent film material may accommodate force-based touch-based screens (e.g.: resistive touch-based screens). Alternatively, capacitive touch-based screens may not require flexibility for operations. In such a scenario, the transparent film material may be integrated to the touch-based screen. An example scenario may be replacing the external glass surface of a touch-based screen with the transparent film material. Additionally, the transparent film material may be glued to the touch-based screen with glue having optical properties to ensure reflective conditions. The transparent film material may also be separated by air from the touch-based screen.

In yet another embodiment, a disinfection controller on a device associated with the touch-based screen may monitor and manage predetermined events to engage and disengage the UV light sources to disinfect the external surface of the transparent film material. A predetermined event may be an expiration of a timer triggering the UV light sources to disinfect. Another predetermined event may be a number of touch-based interactions since a last disinfection. Yet another predetermined event may be a user session. An example may be a user login into and user logout out of the device. Another example of the predetermined event may be the UV light sources being coupled to the activation cycle of the touch-based screen's backlight.

The different processes and systems discussed in FIGS. 1 through 3 may be implemented using distinct hardware modules, software modules, or combinations of hardware and software. Furthermore, such modules may perform two or more of the processes in an integrated manner. While some embodiments have been provided with specific examples for automatically disinfecting a touch-based screen, embodiments are not limited to those. UV and visible light transparent film material may be used to disinfect variety of surfaces subject to user contact including but not exclusive to toilet surfaces, kitchen counters, door knobs, etc. Indeed, embodiments may be implemented in various surfaces using a variety of devices and applications and with additional or fewer features using the principles described herein.

Figure 4:
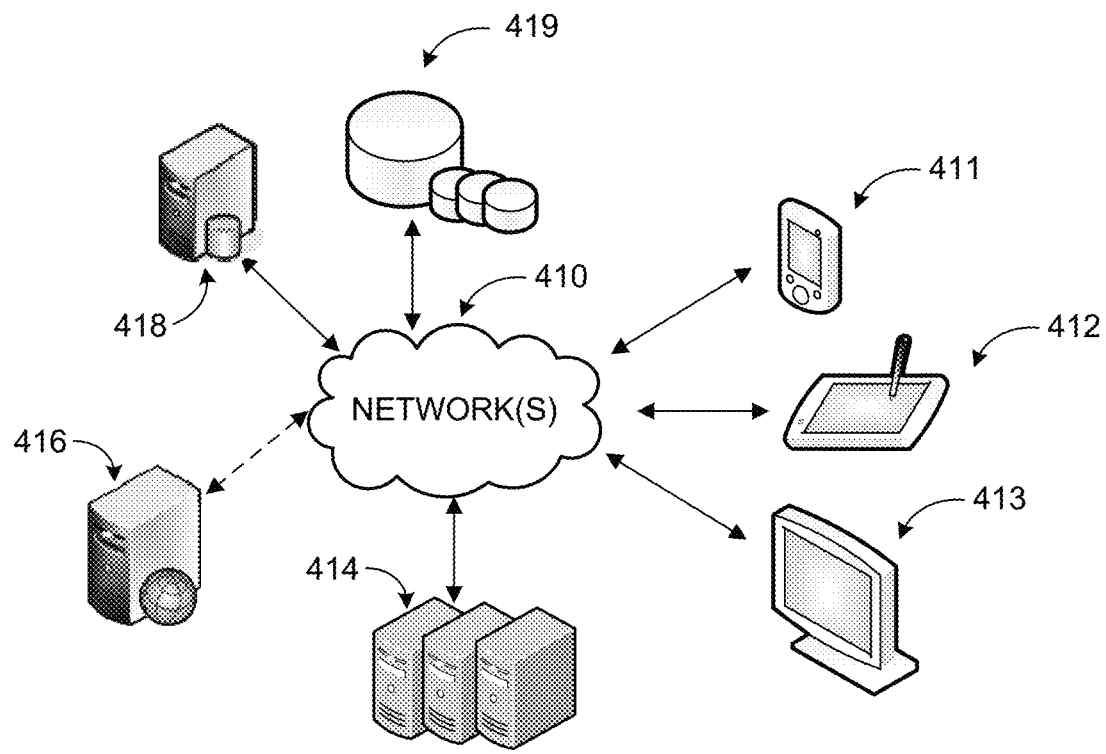
FIG. 4 is a networked environment, where a system according to embodiments may be implemented.

FIG. 4 is an example networked environment, where embodiments may be implemented. A platform for automatically disinfecting a touch-based screen may be implemented via software executed over one or more client applications on individual devices such as a smart phone 411, a tablet 412, a monitor 413, or similar devices ('client devices') through network(s) 410.

Client applications executed on any of the client devices 411-413 may interact with a hosted service providing communication services from the servers 414, or on individual server 416. The hosted service may measure and store metrics such as frequency and length of activation of UV disinfection on client devices. Stored metrics may be used to improve UV disinfection activation time and length by providing UV light source activation parameters to client devices. Some or all of the metrics analysis may be performed at one of more of the servers 414 or 416. Relevant data such as UV light source activation metrics data may be stored and/or retrieved at/from data store(s) 419 directly or through database server 418.

Network(s) 410 may comprise any topology of servers, clients, Internet service providers, and communication media. A system according to embodiments may have a static or dynamic topology. Network(s) 410 may include secure networks such as an enterprise network, an unsecure network such as a wireless open network, or the Internet. Network(s) 410 may also include (especially between the servers and the mobile devices) cellular networks. Furthermore, network(s) 410 may include short range wireless networks such as Bluetooth or similar ones. Network(s) 410 provide communication between the nodes described herein. By way of example, and not limitation, network(s) 410 may include wireless media such as acoustic, RF, infrared and other wireless media.

Many other configurations of computing devices, applications, data sources, and data distribution systems may be employed to implement a platform automatically disinfecting a touch-based screen. Furthermore, the networked environments discussed in FIG. 4 are for illustration purposes only. Embodiments are not limited to the example applications, modules, or processes.

Figure 5:
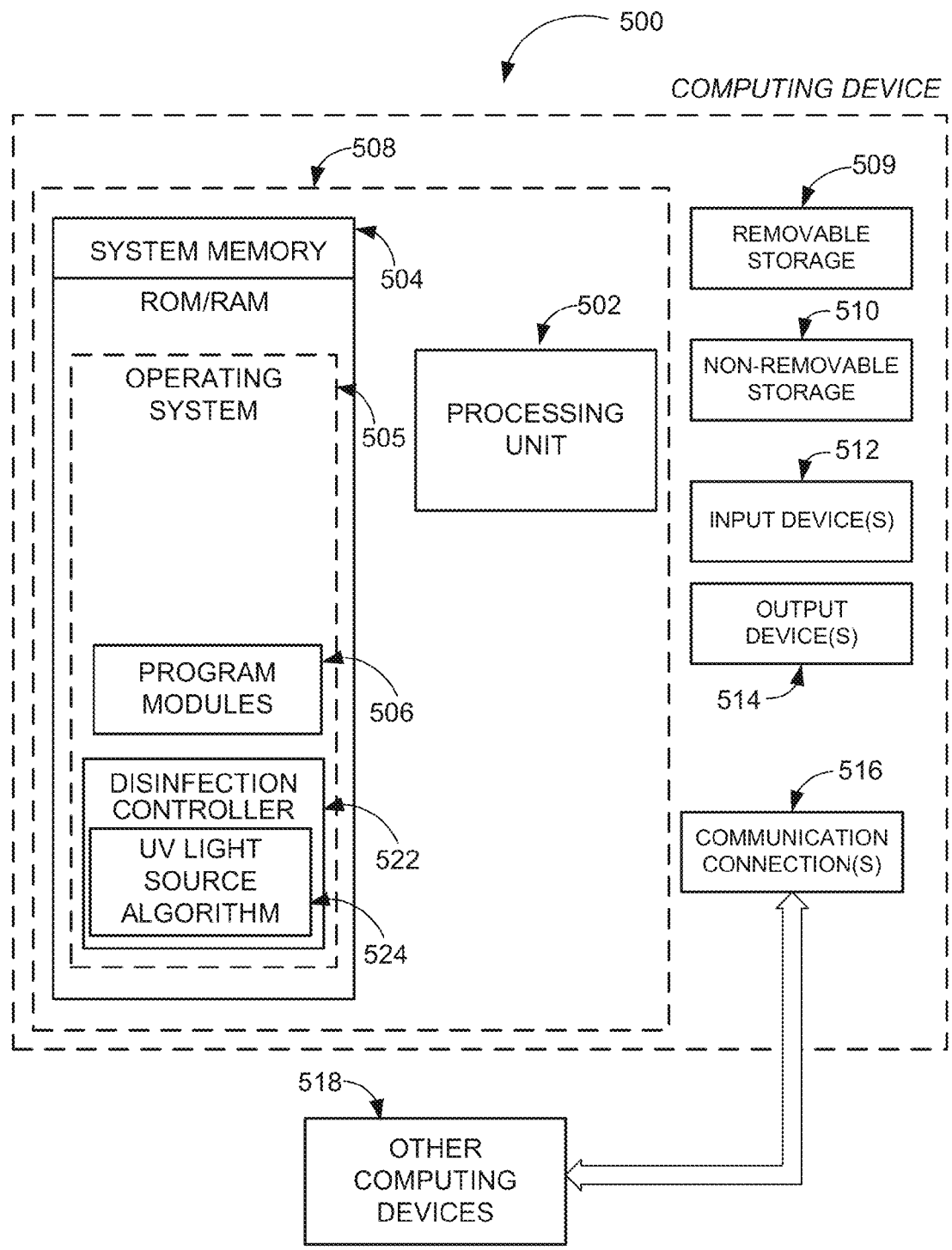
FIG. 5 is a block diagram of an example computing operating environment, where embodiments may be implemented.

FIG. 5 and the associated discussion are intended to provide a brief, general description of a suitable computing environment in which embodiments may be implemented. With reference to FIG. 5, a block diagram of an example computing operating environment for an application according to embodiments is illustrated, such as computing device 500. In a basic configuration, computing device 500 may be a device capable of automatically disinfecting a touch-based screen using a UV light emitted through a transparent film material according to embodiments and include at least one processing unit 502 and system memory 504. Computing device 500 may also include a plurality of processing units that cooperate in executing programs. Depending on the exact configuration and type of computing device, the system memory 504 may be volatile (such as RAM), non-volatile (such as ROM, flash memory, etc.) or some combination of the two. System memory 504 typically includes an operating system 505 suitable for controlling the operation of the platform, such as WINDOWS®, WINDOWS MOBILE®, WINDOWS PHONE®, or similar operating systems from MICROSOFT CORPORATION of Redmond, Wash. or similar ones. The system memory 504 may also include one or more software applications such as program modules 506, disinfection controller 522, and UV light source algorithm 524.

Disinfection controller 522 may turn on and off UV light source(s) to automatically disinfect an external surface of a transparent film material secured onto a display surface of a touch-based screen. UV light source algorithm 524 may manage and determine when and how long to enable the disinfection. Disinfection controller 524 may enable the UV light sources upon detecting contact with the touch-based screen. The disinfection controller 524 may continue the UV light source activation through a predetermined period or through the conclusion of user interaction with the touch-based screen. This basic configuration is illustrated in FIG. 5 by those components within dashed line 508.

Computing device 500 may have additional features or functionality. For example, the computing device 500 may also include additional data storage devices (removable and/or non-removable) such as, for example, magnetic disks, optical disks, or tape. Such additional storage is illustrated in FIG. 5 by removable storage 509 and non-removable storage 510. Computer readable storage media may include volatile and nonvolatile, removable and non-removable media implemented in any method or technology for storage of information, such as computer readable instructions, data structures, program modules, or other data. System memory 504, removable storage 509 and non-removable storage 510 are all examples of computer readable storage media. Computer readable storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and which can be accessed by computing device 500. Any such computer readable storage media may be part of computing device 500. Computing device 500 may also have input device(s) 512 such as keyboard, mouse, pen, voice input device, touch input device, and comparable input devices. Output device(s) 514 such as a display, speakers, printer, and other types of output devices may also be included. These devices are well known in the art and need not be discussed at length here.

Computing device 500 may also contain communication connections 516 that allow the device to communicate with other devices 518, such as over a wired or wireless network in a distributed computing environment, a satellite link, a cellular link, a short range network, and comparable mechanisms. Other devices 518 may include computer device(s) that execute communication applications, other servers, and comparable devices. Communication connection(s) 516 is one example of communication media. Communication media can include therein computer readable instructions, data structures, program modules, or other data. By way of example, and not limitation, communication media includes wired media such as a wired network or direct-wired connection, and wireless media such as acoustic, RF, infrared and other wireless media.

Example embodiments also include methods. These methods can be implemented in any number of ways, including the structures described in this document. One such way is by machine operations, of devices of the type described in this document.

Another optional way is for one or more of the individual operations of the methods to be performed in conjunction with one or more human operators performing some. These human operators need not be collocated with each other, but each can be only with a machine that performs a portion of the program.

Figure 6:
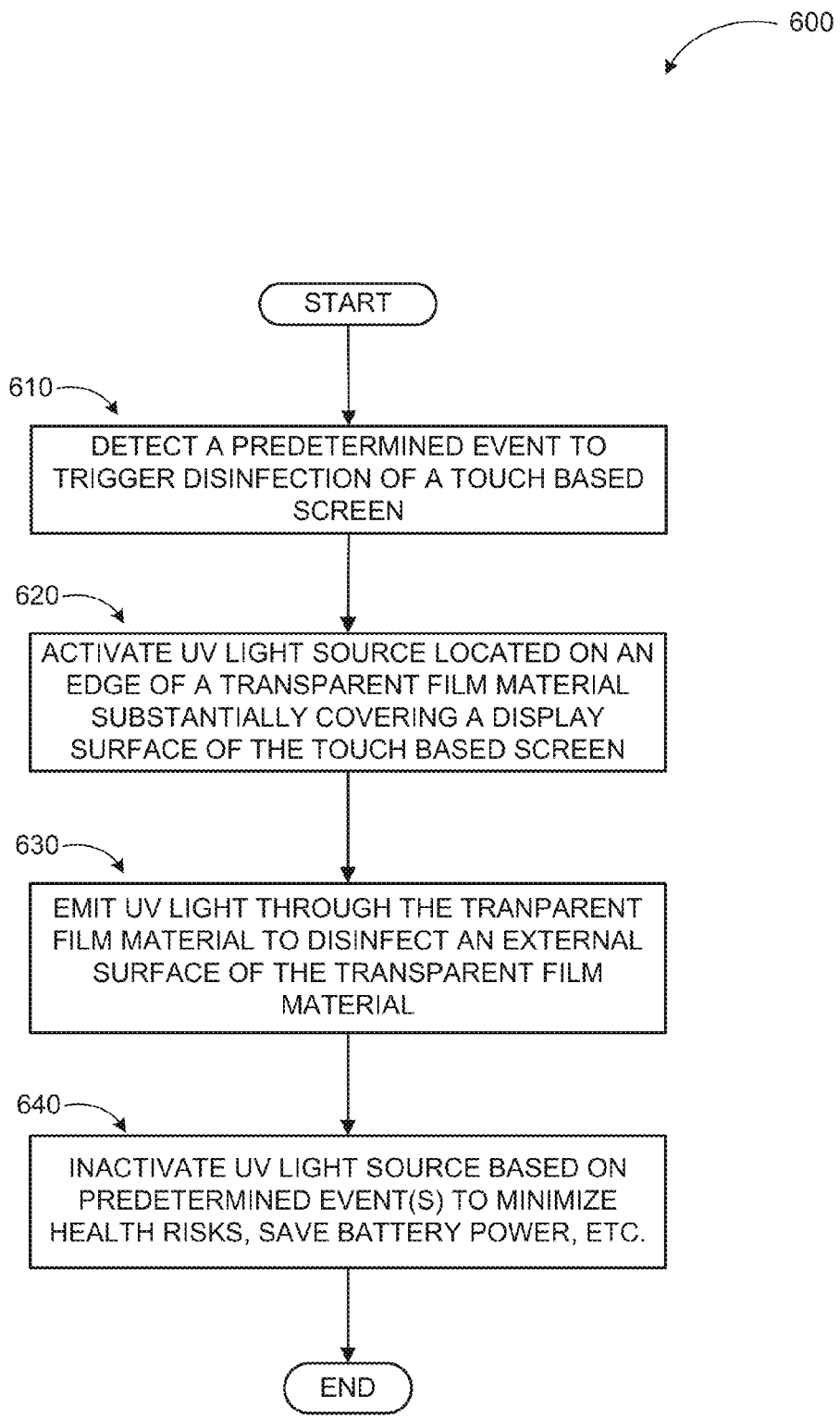
FIG. 6 illustrates a logic flow diagram for automatically disinfecting a touch-based screen.

FIG. 6 illustrates a logic flow diagram for a process 600 of automatically disinfecting a touch-based screen according to embodiments. Process 600 may be implemented on a computing device with an associated touch-based screen.

Process 600 begins with operation 610, where a disinfection controller may detect a predetermined event to trigger disinfection of a touch-based screen. The predetermined event may be a time-based event, user contact, user session trigger, etc. Upon detecting the predetermined event, the disinfection controller may activate a UV light source located on an edge of a transparent film material substantially covering a display surface of the touch-based screen at operation 620.

At operation 630, the UV light may be emitted through the transparent film material to disinfect the external surface of the transparent film material. The UV light may be emitted at a critical angle to contain the UV light within the transparent film material and reflect the light back into the transparent film material. Some of the UV light may exit the transparent film material when the external surface may be contacted by external entities such as fingers. The contact may initiate a disinfection of the fingertips and immediate surrounding areas through the FTIR effect.

Operation 630 may be followed by operation 640, where the UV light source may be disengaged or inactivated based on predetermined events such as expiration of a timer to minimize health risks by limiting exposure, save battery power, etc.

The operations included in process 600 are for illustration purposes. Automatically disinfecting a touch-based screen may be implemented by similar processes with fewer or additional steps, as well as in different order of operations using the principles described herein.

The above specification, examples and data provide a complete description of the manufacture and use of the composition of the embodiments. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims and embodiments.

What is claimed is:

1. An apparatus to automatically disinfect a touch-based screen, the apparatus comprising:
   a transparent film material substantially covering a display surface of the touch-based screen;
   an ultra violet (UV) light source located on an edge of the transparent film material, wherein UV light from the UV light source is emitted through the transparent film material to disinfect the transparent film material such that when a user touches the transparent film material at a contact point, the UV light exits the transparent film material and disinfects fingertips of the user and immediate surrounding areas of the fingertips at the contact point; and
   an optical index matching gel applied between the UV light source and the edge of the transparent film material to allow additional UV light to enter the transparent film material at a low power to maximize safety.

2. The apparatus of claim 1, wherein the transparent film material is separated by air from the touch-based screen.

3. The apparatus of claim 1, wherein the transparent film material is secured to the touch-based screen with an adhesive having one or more optical properties.

4. The apparatus of claim 1, wherein the UV light source is one of a light emitting diode (LED) and a mercury discharge lamp.

5. The apparatus of claim 1, further comprising:
   a layer of flexible material on top of an external surface of the transparent film material, wherein the flexible material is configured to improve transfer of the UV light from the transparent film material.

6. The apparatus of claim 1, wherein the UV light source is configured to emit the UV light in an about 200 nm to about 300 nm wavelength range through the transparent film material.

7. The apparatus of claim 1, further comprising:
one or more optical apertures configured to contain the UV light within the transparent film material.

8. A computing device to automatically disinfect a touch-based screen, the computing device comprising:
a memory; and
a processor coupled to the touch-based screen and the memory, the processor adapted to execute a disinfection controller that is configured to:
detect a predetermined event to trigger disinfection of the touch-based screen;
activate an ultra violet (UV) light source located on an edge of a transparent film material substantially covering a surface of the touch-based screen, the UV light source configured to emit UV light through the transparent film material to disinfect an external surface of the transparent film material, wherein
an optical index matching gel applied between the UV light source and the edge of the transparent film material allows additional UV light to enter the transparent film material at a low power to maximize safety, and
the UV light exits the transparent film material and disinfects fingertips of a user and immediate surrounding areas of the fingertips in response to one of: a contact of the fingertips of the user on the external surface of the transparent film material and a near proximity of the fingertips of the user to the external surface of the transparent film material;
and
disengage the UV light source based on another predetermined event to maintain safe exposure limits.

9. The computing device of claim 8, wherein the transparent film material is secured onto an external surface of the touch-based screen.

10. The computing device of claim 8, wherein the transparent film material is secured to a display surface of the touch-based screen employing an adhesive having optical properties to ensure reflective conditions.

11. The computing device of claim 8, wherein the transparent film material is integrated to an external surface of the touch-based screen.

12. The computing device of claim 8, wherein the processor is further configured to:
couple the predetermined event to an activation cycle of a backlight of the touch-based screen.

13. The computing device of claim 8, wherein the predetermined event is an expiration of a timer.

14. The computing device of claim 8, wherein the predetermined event is a number of touch-based interactions since a last disinfection.

15. The computing device of claim 8, wherein the predetermined event includes a user session.

16. The computing device of claim 15, wherein the user session based event includes a user login and logout in a device associated with the touch-based screen.

17. A computer-readable memory device with instructions stored thereon to automatically disinfect a touch-based screen, the instructions comprising:
detecting a predetermined event to trigger disinfection of the touch-based screen;
activating an ultra violet (UV) light source located on at least one edge of a transparent film material substantially covering a display surface of the touch-based screen, the UV light source configured to emit UV light through the transparent film material to disinfect an external surface of the transparent film material, wherein
an optical index matching gel applied between the UV light source and the at least one edge of the transparent film material allows additional UV light to enter the transparent film material at a low power to maximize safety, and
the UV light exits the transparent film material and disinfects fingertips of a user and immediate surrounding areas of the fingertips in response to one of: a contact of the fingertips of the user on the external surface of the transparent film material and a near proximity of the fingertips of the user to the external surface of the transparent film material; and
disengaging the UV light source based on another predetermined event.

18. The computer-readable memory device of claim 17, wherein a transfer of the UV light from the transparent film material to the fingertips of the user and the immediately surrounding areas of the fingertips of the user is enhanced by an additional layer of flexible material on top of an external surface of the transparent film material enabling behavior similar to liquid in immersion optics.

19. The computer-readable memory device of claim 17, wherein the instructions further comprise:
employing at least one optical aperture to contain the UV light within the transparent film material.

20. The computer-readable memory device of claim 17, wherein the instructions further comprise:
determining a critical angle for the UV light to reflect the UV light back into the transparent film material through total internal reflection effect.

* * * * *